United States Patent [19]
Tekkanat et al.

[11] Patent Number: 5,001,935
[45] Date of Patent: Mar. 26, 1991

[54] METHOD AND APPARATUS FOR DETERMINING THE ENVIRONMENTAL STRESS CRACK RESISTANCE OF PLASTIC ARTICLES

[75] Inventors: Bora Tekkanat; Alan A. Kovacich, both of Milwaukee; Bryan L. McKinney, Shorewood; William H. Tiedemann, Cedarburg, all of Wis.

[73] Assignee: Hoover Universal, Inc., Ann Arbor, Mich.

[21] Appl. No.: 485,585

[22] Filed: Feb. 27, 1990

[51] Int. Cl.$^5$ ............................................. G01N 19/08
[52] U.S. Cl. .................................... 73/799; 73/37
[58] Field of Search ............... 73/799, 37.5, 37, 840, 73/849

[56] References Cited

U.S. PATENT DOCUMENTS

| | | |
|---|---|---|
| 3,710,616 | 1/1973 | Smith et al. |
| 4,107,979 | 8/1978 | Saeda et al. |
| 4,285,230 | 8/1981 | Hartness ............... 73/37 X |
| 4,829,839 | 5/1989 | Fisher et al. ............... 73/866 |

FOREIGN PATENT DOCUMENTS

32843  2/1984  Japan .................................... 73/799

OTHER PUBLICATIONS

ASTM-D-2561-70, "Standard Test Method for Environmental Stress-Crack Resistance of Blow-Molded Polyethylene Containers", pp. 302-307 (Reapproved 1984).

Primary Examiner—Jerry W. Myracle
Attorney, Agent, or Firm—Foley & Lardner

[57] ABSTRACT

A method and apparatus for determining the environmental stress crack resistance of plastic articles, such as polyethylene terephthalate containers, are provided. In accordance with the method of the invention, the internal chamber of a hollow plastic article is pressurized, the exterior of the base is then exposed to an environmental stress cracking agent, and it is then determined if crazing and/or changes in the base clearance of the plastic article have occurred. Subsequent increases in pressure and subsequent exposures and determinations yield information on the environmental stress cracking characteristics of the container.

18 Claims, 5 Drawing Sheets

METHOD AND APPARATUS FOR DETERMINING THE ENVIRONMENTAL STRESS CRACK RESISTANCE OF PLASTIC ARTICLES

TECHNICAL FIELD

This invention relates to a method and apparatus for measuring the environmental stress crack resistance (E.S.C.R.) of plastic articles, such as blow molded polyethylene terephthalate containers.

BACKGROUND OF THE INVENTION

When a plastic material is used in a useful article, such as a container, it is subjected to many types of stress. Stress can be caused by external factors, by deforming forces applied to the material, or by strain which remains in the material from the time of its fabrication. Additionally, the environment to which the material is exposed, i.e. gaseous or liquid, can worsen the effects of stress on the material. This latter phenomenon is environmental stress cracking.

Certain environmental factors cause materials, e.g., plastic articles, to exhibit failure, generally by cracking, at stesses lower than those which cause cracking in the material under ideal (normal) circumstances. Crazing is a precursor to environmentally induced stress cracking. Generally, crazing is caused by the reaction of the material to the environmental factors, in combination with stresses existing within the material or which are applied to the material.

Environmental stress cracking is often the life limiting mode of failure for polymer systems under stress, such as in the case with blow-molded polyethylene terephthalate (PET) beverage containers. Therefore, it is important in the production and use of plastic articles to minimize environmental stress cracking. The design of a plastic article is particularly important where the end use or handling of such article is likely to involve contact with materials known to promote environmental stress cracking.

Blow molded PET containers are widely used in the beverage industry. Particularly well-known are two-liter containers formed of blow molded PET, which serve as containers for beverages of all kinds, e.g., soft drinks. It is especially important to minimize environmental stress cracking for such containers. Major soft drink manufacturers and the ultimate consumers desire containers which will be free, or substantially free, of the tendency to develop environmental stress cracking.

Heretofore PET containers, such as the aforementioned containers for soft drinks, have been constructed in a two-liter configuration. The bottle portion thereof has been blow molded such that there is a narrow neck having an upper mouth, a rounded (e.g., hemispherical) base and a cylindrical sidewall therebetween. Inasmuch as containers having a rounded base cannot stand upright, containers such as these often include a boot or base platform into which the container fits. The boot is typically made of a different kind or grade of plastic.

Containers having two distinct pieces are undesirable from a manufacturing standpoint. Moreover, recycling of two-piece bottles is more difficult than for one-piece containers. It is therefore desirable to have one-piece containers which are capable of standing, without the need for a boot.

A one-piece container requires that the base thereof be molded in a manner that permits it to stand on its own. Such molding, however, tends to increase the susceptibility to crazing and eventual failure. While crazing is not as prevalent in those portions of plastic articles which have been stretched (due to the highly oriented nature of the molecules in those regions), crazing is more likely to occur in areas where there is no noticeable or substantial orientation, such as are caused by the molding of the bottom portion of stand-alone PET containers.

When containers of this type are filled with soft drinks, they are typically pressurized to between about 60 and about 65 psi. Increases in temperature can cause the internal pressure to, at times, reach 90 to 95 psi or more. Such pressure not only affects initiation of crazing, but also affects distortion of the container shape. Again, such distortions are typically noted in areas where the plastic has been unoriented, i.e., particularly at or close to the center of the container base. This pressure-induced distortion also gives rise to crazing, and eventual cracking of the bottle. In particular, the more the bottle is distorted, the greater the possibility of crazing and eventual failure. In general, for PET articles such as sheets, 5% to 7% elongation is a critical point for craze initiation. It is not easy to determine the amount of localized elongation (or strain) in formed articles, such as the one-piece, stand-alone containers described above.

In addition to stress level and environment, there are several factors which can affect the environmental stress crack resistance of PET containers. These factors include, among others, processing conditions and container design. Inasmuch as the environments which cause crazing cannot always be avoided, materials, process conditions, and especially container design must be optimized with environmental stress crack resistance in mind.

Known methods for determining the tendency of plastic articles to undergo environmental stress cracking include tensile load methods, such as the so called Lander Test (ASTM-D-2552). Other standard tests include ASTM-D-1963-60T, wherein a test sample is nicked with a razor blade, bent into a U-shaped configuration and submerged into a solution of a stress cracking agent.

Methods have also been described for determining the environmental stress crack resistance of polymer articles. These involve the external application of stress to an unstressed test article which has been exposed to a stress cracking agent, such as by means of a weight. See, Fisher, et al., U.S. Pat. No. 4,829,839 issued May 16, 1989. Other methods describe the use of a weighted rod which stresses a plastic article in contact with a stress cracking agent in an electrically conductive liquid until the liquid penetrates the stress cracks. See, Smith, et al., U.S. Pat. No. 3,710,616 issued Jan. 16, 1973. Another method includes initially deforming a test piece in a test environment followed by the application of additional stress of a magnitude smaller than that of the stress already produced in the test piece, until the test piece fractures. See, Saeda, et al., U.S. Pat. No. 4,107,979 issued Aug. 22, 1978. These methods are unsuitable for determining the environmental stress crack resistance of blow molded PET containers.

Heretofore such containers have been tested by filling the container with a carbonated beverage under an internal pressure, exposing the container to a line lubricant or other environmental stress cracking agent, and then measuring the time it takes for the container to explode or otherwise show signs of deformation. It is also known to pressurize the container, expose it to acetone or another environmental stress cracking agent, and then pressurize the container until failure occurs.

ASTM-D-2561-70, entitled "Standard Test Methods For Environmental Stress-Cracked Resistance Of Blow-Molded Polyethylene Containers", discloses three procedures for measuring the environmental stress crack resistance of containers made from polyethylene and subjected to an ESC agent, internally in most cases. Each of the procedures is continued until failure, defined as "the formation of any imperfection, such as a crack, which results in a loss of pressurizing gas or stress cracking agent" is observed. These tests are unsuitable for PET containers because, in the test procedure, the container is subjected to the test method until the container has fractured. To fully measure the environmental stress crack resistance of PET containers, it is necessary to collect data on the performance of the container under conditions which exist well before the container fractures. Particularly, preventing conditions which could eventually lead to a fracture is important in the container industry, and ASTM-D-2561-70 does not address that problem.

While some information can be obtained by subjecting blow molded PET containers to the foregoing tests, the tests are unsuitable inasmuch as the results are often difficult to interpret or take too long to obtain. The way such tests are carried out also does not provide information that can be directly correlated to actual field failures. Moreover, the foregoing tests fail to appreciate the phenomenon of crazing, and thus fail to appreciate the significance of information and data which can be obtained when crazing begins.

SUMMARY OF THE INVENTION

The present invention provides a method and apparatus for determining the environmental stress crack resistance of plastic articles. In accordance with the method of the invention, the internal chamber of a hollow plastic article is pressurized, the exterior base of the article is exposed to an environmental stress cracking agent, and it is then determined if crazing of the plastic article has occurred. For purposes of the invention, "crazing" refers to regions of plastic (permanent) deformation normal to the direction of the applied load, i.e., the force causing stress. Crazes can be observed visually as small streaks in the plastic which can ultimately become complete cracks. Subsequent increases in pressure and subsequent exposures and determinations can be used to yield information on the environmental stress cracking characteristics of the container in question, particularly the threshold pressure at which crazing (and, hence, stress cracking) is likely to occur.

An apparatus for carrying out this method is also provided. The apparatus comprises a device for sealing the mouth of a hollow plastic article, a supply of pressurized gas, and suitable means for exposing the article externally to an environmental stress cracking agent.

In accordance with another aspect of the method of the invention, the base clearance of the article is measured to determine if the article has undergone any deformation as a result of the foregoing method. An apparatus for measuring base deformation according to the invention includes a gauge mounted in a housing which receives the lower end of a container having an inverted base. The probe of the gauge is displaced by an amount which indicates the base clearance of the container.

In accordance with a further aspect of the invention, the above-referenced method and apparatus can be used to collect data which can be extremely useful in designing a container which is resistive to environmental stress cracking.

DETAILED DESCRIPTION OF PREFERRED EMBODIMENTS

It has been found in accordance with the invention that hollow plastic articles, such as blow-molded polyethylene containers, can be tested to determine the environmental stress crack resistance of the article in a simple, efficient and productive manner, the results of which provide beneficial information for the design of such articles.

In accordance with the method and apparatus of the invention, a hollow container is tested to determine its environmental stress crack resistance. Preferably, with reference to FIG. 1, the container comprises a PET container (bottle) 10. Container 10 can be formed of any suitable plastic, such as polypropylene, polyethylene, polyvinyl chloride (PVC), polystyrene, acrylonitrile-butadiene-styrene (ABS), acrylonitrile-styrene (ANS), polycarbonates, polyethylene terephthalate (PET) and blends thereof. Preferably, for purposes of illustrating the invention, container 10 comprises a blow-molded polyethylene terephthalate one-piece container. While the invention will be described herein below in conjunction with such a container, it should be appreciated that other plastic articles and shapes are within the scope of the invention.

Figures 1, 2:
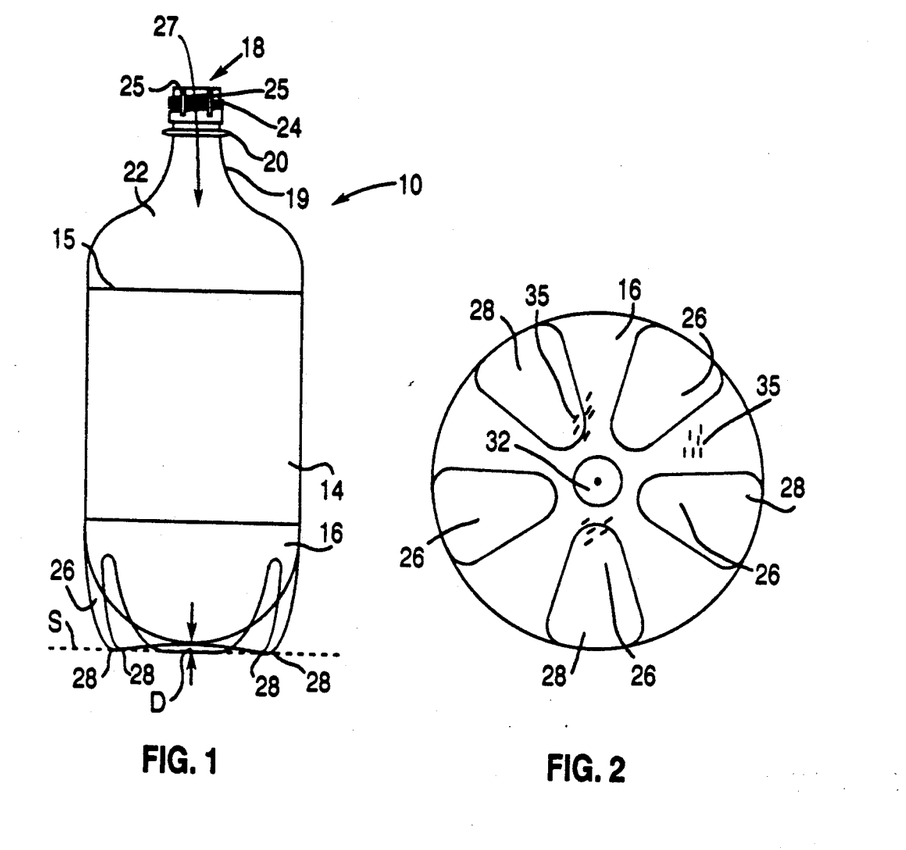
FIG. 1 is a perspective view of a plastic container which may be tested by the method and apparatus of the invention.
FIG. 2 is, a bottom view of the container shown in FIG. 1, with crazes illustrated.

Container 10 comprises a top section 12, a rounded base 16, and a generally cylindrical midsection 14 spanning top section 12 and base 16. A label 15 is adhesively applied to the outside of midsection 14. Top section 12 includes a generally arcuate shoulder 22 which extends from midsection 14 and tapers to form a narrow neck 19 which ends in a circular mouth 18. The upper end of neck 19 adjoining mouth 18 has threads 24, air vents 25, and radial lip (flange) 20 for engaging a cap. Container 10 is hollow with thin walls, and thus has an internal chamber 27 which holds a liquid, such as a soft drink.

Base 16 enables container 10 to stand upright without the need for a boot or other attachment. Base 16 commonly includes a plurality of generally triangular feet 26 configured so that outer ends (toes) 28 thereof are ranged about the outer periphery of base 16. Toes 28 contact the surface S upon which container 10 stands. With reference to FIG. 2, outer toes 28 are disposed near the periphery of base 16, which is substantially equivalent in diameter to midsection 14. Inwardly of feet 26 lies an inverted central base spot (center) 32. Center 32, is typically circular or slightly hemispherical, but may take other shapes. The vertical distance between center 32 and the plane of outer toes 28 is base clearance D of container 10.

Figure 3:
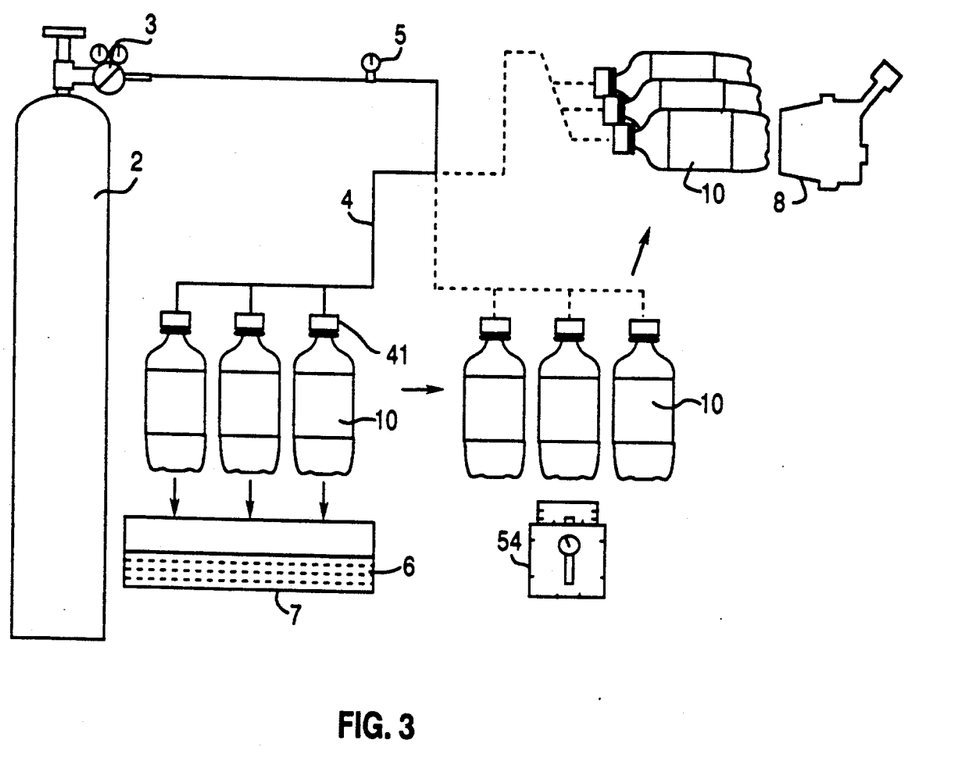
FIG. 3 is schematic diagram of an apparatus according to the invention.

Referring to FIG. 3, according to a method of the invention, one or more containers 10 are first filled nearly full of a clear liquid, such as water. Although water acts as a crazing agent when the exterior of container 10 is exposed thereto, no such effect is observed when water contacts container 10 from the inside because the inner surface is under pressure, i.e., compression where crazing is likely to occur. Water is a suitable filler liquid for the test, even if the commercial product will be a beverage.

One or more containers 10 are then connected to test apparatus 1 and pressurized with any suitable gas. Preferably, nitrogen is supplied to chamber 27 of each container 10 through mouth 18. Pressurized nitrogen is fed from a conventional pressurized nitrogen tank 2 having a pressure regulator 3 through a flexible hose or tube 4 provided with a pressure gauge 5. A branch of tube 4 enters each mouth 18 through a suitable pressure sealing cap assembly 41. A cap assembly 41A or 41B as depicted in FIGS. 5A or 5B may be utilized.

Figure 5A:
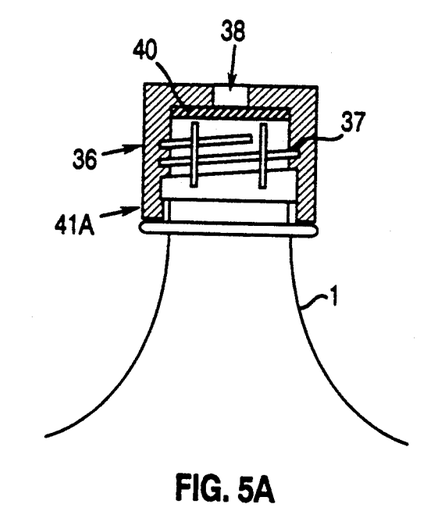
FIG. 5A is a side view, partly in section, of the top of a container provided with a pressure injection assembly according to the invention.

A cap assembly 41A of FIG. 5A includes an aluminum cap 36 through which a hole 38 is drilled. A rubber washer 40 is provided between the rim of mouth 18 and bottom of cap 36. Cap 36 is secured to mouth 18 by threads 37 which correspond to threads 24 on container 10. A tube connected to a source of nitrogen under pressure (e.g., tank 2) is inserted into hole 38 and frictionally secured therein.

Figure 5B:
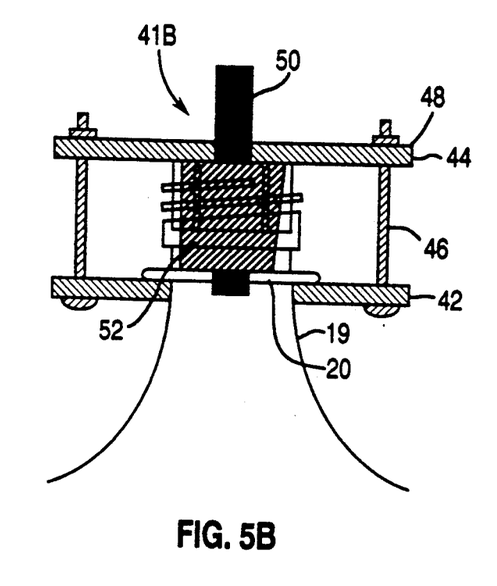
FIG. 5B is a view similar to FIG. 5A, but showing an alternative embodiment of a cap assembly according to the invention.

Alternatively, a cap assembly 41B, such as depicted in FIG. 5B, may be employed. This preferred, alternative cap assembly includes a lower plate 42 which is affixed to an parallel, spaced-apart, upper plate 44 by screws 46 and nuts 48. Lower plate 42 has a groove therein in which neck 19 closely fits. Upper plate 44 has a similar groove (or hole) of slightly greater diameter than a swaged brass tube 50. Tube 50 extends through a rubber stopper 52 which plugs mouth 18. Plates 42, 44 clamp down stopper 52. Cap assembly 41B thereby seals mouth 18 and permits pressurization of container 10.

Referring again to FIG. 3, each container 10 is then pressurized to an initial pressure, generally between about 5 to about 15 psi, preferably to about 10 psi. Once each container 10 is pressurized, base 16 of each container 10 is immersed in the environmental stress cracking agent (water) 6 in a pan 7. In general, stress cracking agents useful in the method of this invention include fats, oils, greases, and organic solvents, such as aromatic hydrocarbons, alcohol, acetone and the like, water, smf lubricants, such as line lubricants. However, any substance which acts as a solvent or softening agent for the plastic, i.e. which lowers intermolecular bonding of the plastic, may be utilized as the stress cracking agent. Preferably, the environmental stress cracking agent is water, a lubricant (i.e., aqueous surfactant solution), an alcohol or acetone.

Once the container is exposed to the stress cracking agent, containers 10 are removed from pan 7 while still connected to hose 4 and examined with a stereomicroscope 8 to determine if crazing has taken place. Base 16 can also be examined for crazing by other suitable means, such as visual inspection, acoustic techniques, or interference microscopy. A stereomicroscope having zoom capability ranging from 8 to 30 times magnification, together with a light source for illuminating the base of the container 10, is preferred. FIG. 2 illustrates groups of crazes 35 in positions near center 32 at which crazing typically occurs in such containers 10. A camera may be used to record the nature and location of the crazes observed.

Before or after inspecting containers 10 for crazes, each container 10 may be inserted into a base clearance gauge 54 to determine the base clearance distance D of that container 10 at the current pressure. As described hereafter, large changes in base clearance at lower pressures, such as 1-20 psi, coincide with low craze initiation thresholds at higher pressures.

Figure 6A:
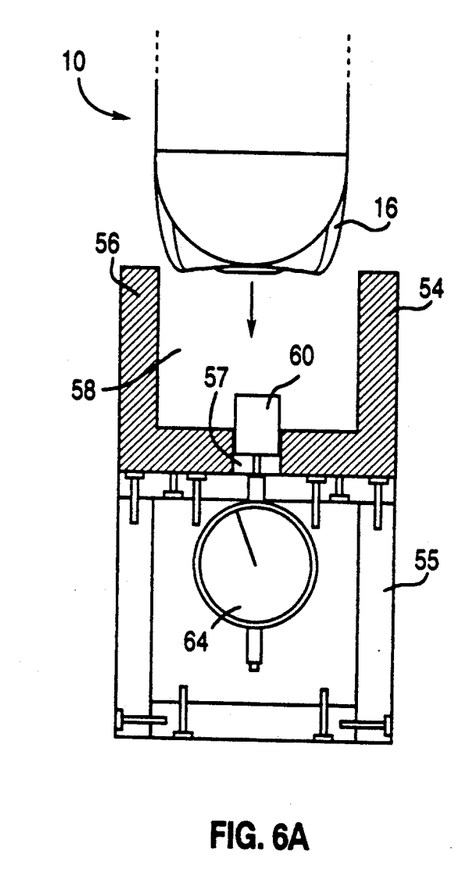
FIG. 6A is a perspective view, partly in section, of a base; clearance gauge of the present invention.
Figure 6B:
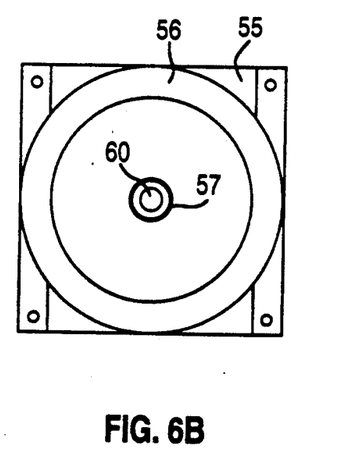
FIG. 6B is a top plan view of the gauge shown in FIG. 6A.

Referring to FIGS. 6A and 6B, base clearance gauge 54 preferably includes a cylindrical holder 56 mounted on top of a supporting frame 55. Holder 56 has a round upper opening 58 for closely receiving base 16 of container 10. A cylindrical probe 60 extends into housing 56 through a lower, small central opening 57 in the bottom wall of holder 56. A spring mechanism (not shown) biases probe 60 to an uppermost position. A dial indicator 64 connected to probe 60 converts the axial movement of probe 60 to a visual display. Indicator 64 is mounted on frame 55 beneath holder 56.

Base 16 of container 10 is inserted into opening 58 of base clearance gauge 54. Inverted center 32 of container 10 is thereby placed in mating juxtaposition with measuring device 60. Probe 60 is thus pressed downwardly, and the extent of such movement is indicated by gauge 64 as the base clearance D. Base clearance D may be measured with each incremental increase in pressure. Generally, as pressure increases, the base clearance decreases for most container designs. However, some container designs show an increase in base clearance as the pressure increases. In general, large decreases in base clearance with increasing pressure correlate with an increased likelihood of environmental stress cracking.

After base clearance measurements and inspection for crazing has been completed, containers 10 are reimmersed in water 6, and the pressure in each container is increased by a predetermined increment, such as by from 1-20 psi, most typically 5 or 10 psi. The entire procedure is then repeated at the elevated pressure level. If no crazing is observed, the pressure is increased again. The process continues until a craze initation threshhold pressure can be determined, and may be continued until container 10 actually fails, i.e., cracks. However, a low craze initiation threshold for the type of article being tested generally indicates a correspondingly high rate of failure. For this reason, it is unnecessary to increase the pressure to a level at which an explosion actually results. In one embodiment of the invention, chamber 34 of container 10 is first pressurized to an initial pressure of 10 psi, and thereafter the pressure is increased by 10 psi to a final pressure of 100 psi or more. By testing a number of articles of like design in this fashion, the environmental stress cracking resistance of a particular design can be determined.

To demonstrate the present method, 2-liter PET bottles of nine different designs were tested according to the method of the invention. Each design had a different base configuration. Twelve containers of each design were first filled with tap water. Once filled, cap assemblies were secured over the mouth of each container. The base clearance of each container was determined through use of base clearance gauge 54. The containers were then pressurized in 10 psi increments. After each pressurization, the base of each container was exposed to distilled water as a mild stress cracking agent for approximately three minutes.

The base of each container was then examined to determine if crazing had taken place. Inspection was conducted with an 8× stereo microscope. A high intensity lamp was used to highlight crazes. Inasmuch as crazes have a lower density and a lower refractive index than the surrounding plastic of the container, the stereo-microscope made it possible to detect even small crazes.

The tests of the various types of containers were conducted at room temperature and at about 50% relative humidity. The environmental stress cracking agent, distilled water, was at about 22°±1° C. The pan was of sufficient depth so that approximately two inches of the base of each container were immersed.

Once detected, the regions in which the crazes were identified were diagramed, as illustrated in FIG. 2. In instances where it was difficult to determine if crazing had occurred, the location and appearance of the condition observed was noted, and any such location and condition was checked carefully after further increases in pressure. Since crazes will generally increase in length, depth and number with increasing pressure, while scratches will not, observed aggravation of a suspected craze can confirm whether the initial observed feature was a craze or a scratch.

Craze initiation pressures for each container design were as follows:

| Design | Craze Initiation Pressure (psi) |
| --- | --- |
| 1 | 20.0 |
| 2 | 37.8 |
| 3 | 28.3 |
| 4 | 65.8 |
| 5 | 66.1 |
| 6 | 77.5 |
| 7 | 86.7 |
| 8 | 81.3 |
| 9 | 68.3 |

A craze initiation pressure of at least 60, preferably at least 80, is acceptable for 2-liter PET plastic soft drink containers. Designs 1-3, accordingly, were found to have insufficient environmental stress crack resistance when exposed to water.

Figure 4:
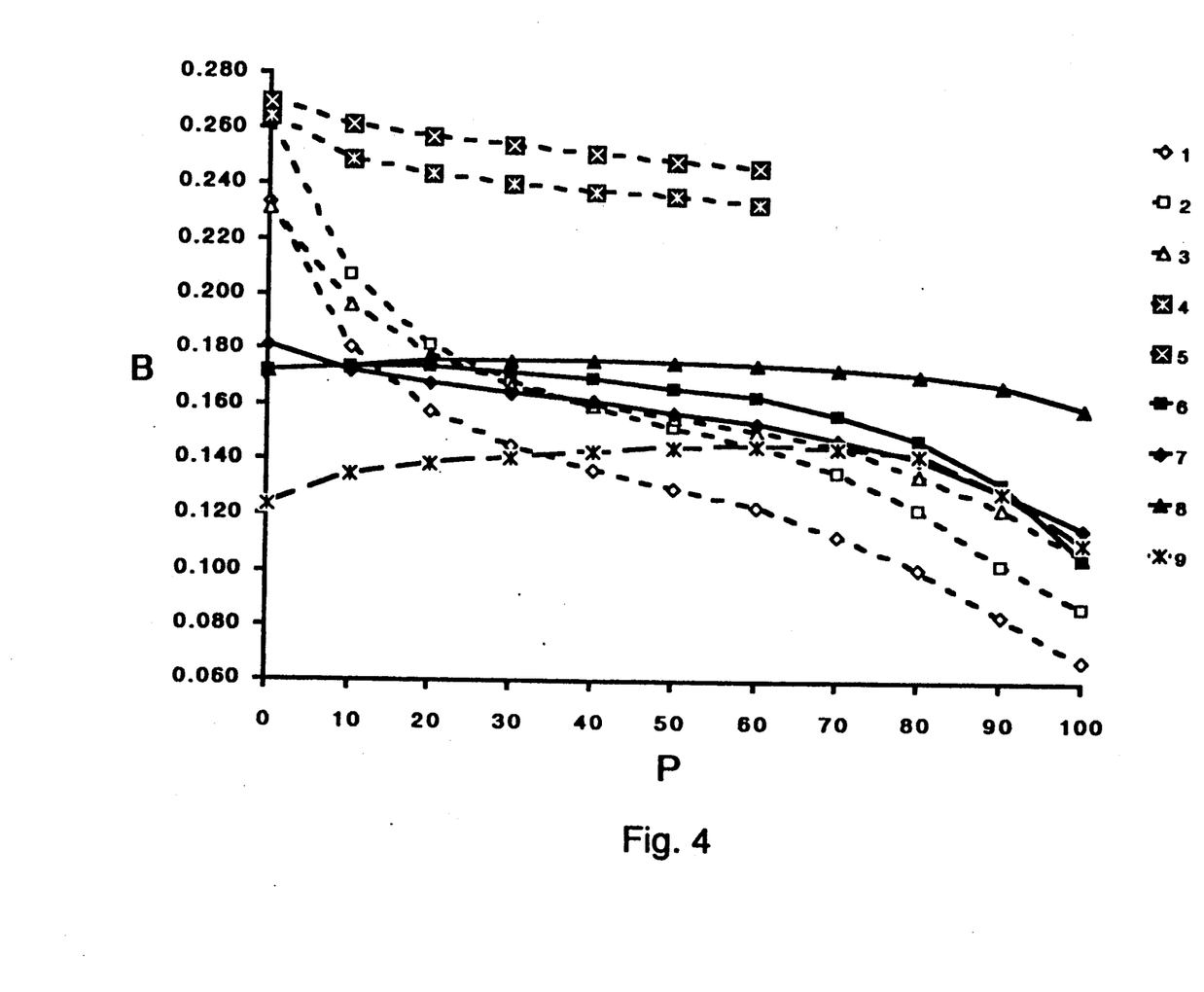
FIG. 4 is a graph showing base clearance (B) in inches vs. versus pressure (P) in psi for nine container types as identified by symbol in the right margin, data for which has been determined according to the method of the invention.

The base clearance results obtained for the various container designs are depicted in FIG. 4. The base clearance, in inches, of each of the different types of containers is plotted with respect to the increase of pressure. The containers of Groups 4 and 5 were incrementally pressurized to a final pressure of 60 psi, while the remaining groups of containers were pressurized to a final pressure of 100 psi. A comparison of the craze initiation pressures with base clearance changes for the nine container designs tested indicated that a substantial decrease in base clearance (e.g., of at least about 0.02-0.04 inch or more) as the container is pressurized from 0 to 20 psi coincides with low craze initiation pressures (compare designs 1-3 with 4-9).

The foregoing results illustrate that craze initiation depends on the internal container pressure. Craze initiation is also dependent upon time and temperature. However, by measuring the pressure, time and temperature effects can be readily derived from the Arhenius equation:

$$1/t = Ae^{(-E_a + BP/RT)}$$

wherein t is craze initiation time, A and B are constants, $E_a$ is activation energy, P is pressure, R is the universal gas constant and T is temperature.

The present invention determines the stress crack resistance of a plastic article by determining the craze initiation pressure of the article. Using this method, the design of the article can be modified to increase craze initiation pressure and reduce changes in base clearance. For example, the design of container type 3 was modified to have less initial base clearance change on the basis of the results shown in FIG. 4. This design change also resulted in a higher craze initiation pressure. Narrowing of the feet of the base, with corresponding widening of the strap areas between the feet, also provided higher craze initiation pressures.

Craze initiation pressure has been found to correlate well with failure rates of the containers in industry, in which a container failure rate of less than 1 per million is required. For example, the container of design 8 has a low failure rate in commercial use, confirming that a craze initiation pressure of at least about 80 psi is acceptable in typical 2-liter plastic beverage containers of the type shown in FIG. 1. By contrast, the excessive failure rate of designs 1, 2 and 3 indicates that a craze initiation pressure of 40 psi or less is unacceptable for standard 2 liter PET soft drink containers. Field experience with container failures thus provides a standard against which craze initiation pressures and/or base clearance changes can be compared in order to evaluate a container's, susceptibility to environmental stress cracking and ultimate failure.

It will be understood that the foregoing description is of a preferred exemplary embodiments of the invention, and that the invention is not limited to the specific forms shown. Plastic articles in configurations other than bottles may be tested. Furthermore, the method of the invention is readily adaptable to mechanical or electronic automation, e.g., by using an optical scanner to locate crazes in lieu of a human observer. The method of the invention can also be used without exposing the plastic article to an environmental stress-cracking agent to evaluate the strength of the article under normal conditions. These and other modifications may be made in the design and configuration of the components without departing from the spirit of the invention as expressed in the appended claims.

What is claimed is:

1. A method for testing the environmental stress cracking resistance of a plastic article having an internal chamber and a mouth allowing filling and emptying of said chamber, said method comprising the steps of:
   (a) pressurizing said chamber;
   (b) exposing said article externally to an environmental stress cracking agent; and
   (c) detecting if crazing has occurred in said article.

2. The method of claim 1, wherein said plastic article is a bottle.

3. The method of claim 2, wherein said bottle has a rounded base, a narrow neck adjoining said mouth, and a generally cylindrical midsection spanning said neck and said base.

4. The method of claim 3, wherein said base has a plurality of feet for supporting said bottle in an upright position, and an inverted center inwardly of said feet.

5. The method of claim 4, wherein said step (c) further comprises inspecting said base proximate said inverted center for crazes.

6. The method of claim 5, further comprising repeating steps (a)–(c) at increased pressure increments until crazing is detected, and comparing the determined craze initiation pressure with a standard to evaluate the susceptibility of said article to environmental stress cracking.

7. The method of claim 6, further comprising a step of measuring the base clearance of said bottle after each pressure increase while maintaining such pressure, wherein said base clearance is the distance between said center of said base and a plane in which said feet lie.

8. The method of claim 1, further comprising repeating steps (a)–(c) at increased pressure increments until crazing is detected, and comparing the determined craze initiation pressure with a standard to evaluate the susceptibility of said article to environmental stress cracking.

9. The method of claim 8, wherein said environmental stress cracking agent is selected from the group consisting of water, aqueous surfactant solutions, alcohols, and acetone.

10. The method of claim 9, wherein said environmental stress cracking agent is water.

11. The method of claim 1, wherein step (a) further comprises partially filling said chamber with a liquid, and then feeding compressed gas into such chamber.

12. The method of claim 1, wherein said step (c) comprises visually observing said article for crazes.

13. A method for testing the environmental stress cracking resistance of a thin-walled, hollow plastic container having an interior chamber, which container comprises a neck having a mouth for filling the interior chamber of the container, a generally cylindrical midsection, and a rounded base at the end of the container opposite the neck, which base has a plurality of feet for supporting the container on a supporting surface in an upright position, and an inverted center radially inwardly of the feet and adjoining said interior chamber, which center is spaced by a base clearance in the lengthwise direction of the container from an imaginary plane passing through toes of each of the feet, which toes contact the supporting surface, which method comprises:

(a) measuring the base clearance of the container;

(b) pressurizing the interior chamber of said container;

(c) remeasuring the base clearance of the container; and (d) comparing the resulting change in base clearance with a standard to determine the susceptibility of said container to environmental stress cracking.

14. The method of claim 13, further comprising repeating steps (a)–(d) at predetermined increments of increased pressure.

15. The method of claim 14, wherein said steps (a)–(d) are repeated at two pressures differing by at least about 5 psi in the range of up to about 20 psi.

16. The method of claim 13, wherein said container is a bottle made of polyethylene terephalate or polyvinyl chloride.

17. An apparatus for measuring a base clearance of a thin-walled, hollow plastic container having an interior chamber, which container comprises a neck having a mouth for filling the interior chamber of the container, a generally cylindrical midsection, and a rounded base at the end of the container opposite the neck, which base has a plurality of feet for supporting the container on a supporting surface in an upright position, and an inverted center radially inwardly of the feet and adjoining said interior chamber, which center is spaced by the base clearance in the lengthwise direction of the container from an imaginary plane passing through toes of each of the feet, which toes contact the supporting surface, which apparatus comprises:

a housing having an upper opening for closely receiving the base of the container;

a measuring probe extending into said housing through a lower opening therein, such that, when said measuring device is placed in mating juxtaposition with the base of the container in engagement with its inverted center, the depth of the inverted center is measured by the extent of downward displacement of said measuring probe; and an indicator connected to said measuring probe for displaying the extent of such downward movement.

18. Apparatus for testing the environmental stress crack resistance of a hollow plastic article having an internal chamber, a mouth for filling and emptying said chamber, a base, and a sidewall spanning said mouth and said base, comprising:

means for sealing said mouth;

means for supplying a pressurized gas into said chamber through said mouth;

means for exposing said article to an environmental stress cracking agent; and means for detecting crazing of said article.

* * * * *